(12) United States Patent
Purvis et al.

(10) Patent No.: US 6,207,423 B1
(45) Date of Patent: Mar. 27, 2001

(54) DENATURATION OF DOUBLE-STRANDED NUCLEIC ACIDS

(75) Inventors: Duncan Ross Purvis, Royston; Philip Nigel Bartlett, Alresford, both of (GB)

(73) Assignee: Scientific Generics Limited, Cambridge (GB)

( * ) Notice: Subject to any disclaimer, the term of this patent is extended or adjusted under 35 U.S.C. 154(b) by 0 days.

(21) Appl. No.: 09/180,501

(22) PCT Filed: May 9, 1997

(86) PCT No.: PCT/GB97/01258

§ 371 Date: May 5, 1999

§ 102(e) Date: May 5, 1999

(87) PCT Pub. No.: WO97/43445

PCT Pub. Date: Nov. 20, 1997

(30) Foreign Application Priority Data

May 10, 1996 (GB) .................................................. 9609815

(51) Int. Cl.[7] .............................. C12Q 1/68; C12Q 19/34; C07H 21/04; C07H 21/02
(52) U.S. Cl. ........................ 435/91.1; 435/91.1; 435/91.2; 536/25.42

(58) Field of Search ............................. 435/6, 91.2, 91.1; 536/25.42; 935/22.28

(56) References Cited

U.S. PATENT DOCUMENTS 5,607,832 * 3/1997 Stanley et al. ........................ 435/6

OTHER PUBLICATIONS

B. Belotserkovskii, "Polypropylene Tube Surfaces May Induce Denaturation and Multimerization of DNA," Science, vol. 271, Jan. 12, 1996, pp. 222–223.

V. Brabec et al., "Interaction of Nucleic Acids with Electrically Charged Surfaces II. Conformational Changes in Double–Helical Polynucleotides," Biophysical Chemistry, vol. 4, (1976) pp. 79–92.

* cited by examiner

Primary Examiner—Stephanie Zitomer
(74) Attorney, Agent, or Firm—Pillsbury Winthrop LLP

(57) ABSTRACT

This invention provides methods for denaturing nucleic acids. The methods involve contacting a solution comprising double stranded nucleic acid with a surface having denaturation activity sufficient to produce denaturation within a period of not more than one hour.

9 Claims, 4 Drawing Sheets

1. $10^4$ target non_denatured
2. $10^4$ target Naflo_denatured 30s
3. Control heat denatured SDA Gel scan showing band intensity SDA after DNA denaturation on Nafion DNA denaturation using pellets of Nafion 1 Water control, 20 minutes 2 Nafion pellets in water, 20 minutes 3 TE control, 20 minutes 4 Nafion pellets in TE, 20 minutes 5 Single stranded DNA control 6 Double stranded DNA control 7 Water control, 60 minutes 8 Nafion pellets in water, 60 minutes 9 TE control, 60 minutes 10 Nafion pellets in TE, 60 minutes

DENATURATION OF DOUBLE-STRANDED NUCLEIC ACIDS

This application is a 371 of PCT/GB97/01258 filed May 9, 1997.

The present invention relates to methods of denaturation of double-stranded nucleic acids and to further processes utilising single-stranded or partially single-stranded nucleic acids produced by such denaturation.

Double-stranded DNA (deoxyribonucleic acid) and RNA/RNA (ribonucleic acid) and DNA/RNA complexes in the familiar double helical configuration are stable molecules that in vitro require aggressive conditions to separate the complementary strands of the nucleic acid. Methods that are commonly employed for strand separation require the use of high temperatures of at last 60° C. and often 100° C. for extended periods of five minutes or more or use an alkaline pH of 11 or higher. Other methods include the use of helicase enzymes such as Rep protein of E.coli that can catalyse the unwinding of DNA in an unknown way, or binding proteins such as 32-protein of E.coli phage T4 that act to stabilise the single-stranded form of DNA. The denatured single-stranded DNA produced by such known processes of heat or the use of alkali is used commonly for hybridisation studies or is subjected to amplification procedures. We have now discovered that the exposure of double-stranded nucleic acids to certain solid surfaces can produce a rapid denaturation or partial denaturation sufficient to allow the resulting wholly or partially single-stranded nucleic acids to take part in hybridisation or amplification procedures.

Belotserkovskii and Johnston, "Science" vol. 271 1996 have disclosed observing some unspecified degree of denaturation of DNA sequences containing multi-repeats of CA or of GA upon incubation in polypropylene macrophage tubes. The denaturation observed appears to be partial only and at a low level despite incubation over several hours. The mechanism by which denaturation occurs is not disclosed. The phenomenon is not sufficiently pronounced to make the single-stranded DNA produced useable in a practicable manner. Also, in a response to the article, Gaillard and Strauss question whether denaturation is responsible for the observed phenomena.

The present invention now provides a method of denaturing or partially denaturing a double-stranded nucleic acid, comprising contacting a liquid containing said double-stranded nucleic acid with a surface having denaturation activity sufficient to produce said denaturation within a period of not more than one hour.

The denaturation normally takes place within a period of not more than 5 minutes, usually much less, e.g. within a period of not more than 1 minute. A few seconds, e.g. about 10 seconds or less is in fact usually sufficient.

The surface may be chosen to have an acidity or basicity sufficient to produce said denaturation.

The invention includes a method of conducting a nucleic acid hybridisation procedure comprising denaturing a double stranded nucleic acid by a method described to produce at least partially single stranded nucleic acid and hybridising a second nucleic acid with the single stranded nucleic acid so produced.

The invention further includes a method of conducting a nucleic acid amplification procedure requiring single stranded nucleic acid, comprising denaturing a double stranded nucleic acid by a method as described to produce at least partially single stranded nucleic acid and conducting said amplification using said single stranded nucleic acid so produced.

Preferably, the surface is acidic. Most acidic ion exchange materials are not sufficiently acidic to produce the desired effect. It is therefore preferred to employ a strongly acidic surface such as may be obtained where acid groups are attached to an electron withdrawing polymer structure. Suitably, the polymer structure comprises fluorine substituted carbon atoms and is for instance a perfluorinated polymer backbone. Preferably, the polymer is a tetrafluoroethylene-perfluoro-2-(fluorosulphonylethoxy) propylvinyl ether. Suitable such materials are commercially available under the Trade Mark NAFION, e.g. NAFION 117. NAFION is available as beads or as membranes or in solution for the casting of membranes. Due to the electron withdrawing effect of the perfluorocarbon backbone, the acidic character of the sulphonic acid groups can be comparable to that of 100% $H_2SO_4$ and trifluoromethanesulphonic acid in trifluoroacetic acid anhydride solution.

Other materials likely to produce the effect are other polysulphonates, sulphonated resins such as DAIS585 a sulphonated styrene/ethylene-butylene/styrene triblock copolymer, or activated polymers such as nylon treated with $H_2SO_4$ and rinsed in distilled water.

The wholly or partially single-stranded nucleic acid produced may be utilised in any desired manner. In particular, it may be reacted in a sequence specific manner with complementary nucleic acid. Such an action may take place in a hybridisation assay or in an amplification procedure. Many procedures are now known for amplifying nucleic acids. All the known procedures require that a double-stranded template or target nucleic acid is initially denatured to wholly or partially single-stranded form. There may be a need to carry out such denaturation repeatedly during the course of the amplification procedure but in some amplification procedures denaturation is required only once at the beginning of the process. The practice of such amplification procedures falls within the scope of this invention if any one denaturation event is conducted by method as described above. Examples of nucleic acid amplification procedures within the scope of the invention include the polymerase chain reaction (PCR) as described in U.S. Pat. No. 4,683,202 and many other publications. It may be a variant of the classical or standard PCR process, e.g. the so-called "inverted" or "inverse" PCR process, an asymmetric PCR process or the so-called "anchored" PCR process. The amplification may be a ligase chain reaction (LCR) as described in Barany Proc. Natl. Acad. Sci. USA, Vol. 88, pp 189–193 - 1991. It may be a Nasba or 3SR process as described in Biotechnology, Vol. 13, June 1995 by Sooknanan et al or in Proc. Natl. Acad, Sci. USA, Vol. 87, pp 1874–1978, March 1990, Biochemistry by Guatelli et al. It may be used in the preparation of samples for branched DNA signal amplification (bDNA) as described in Biotechnology, Vol. 12, September 1994, pp 926–928 by Urdea. The denaturation technique of the invention may also be used in sample preparation for the strand displacement assay (SDA) as described in Proc. Natl. Acad. Sci. USA, Vol. 89, pp 392–396, Applied Biological Sciences, January 1992 by Walker et al and elsewhere. The denaturation technique according to the invention may be used equally in amplification techniques which depend upon amplifying the amount of nucleic acid and techniques which rely upon conducting a hybridisation to a probe providing an amplified detectable signal, e.g. bDNA.

The nucleic acid to be denatured may be dissolved in water or other suitable solvent with or without other ingredients such as buffer materials. A sample of the nucleic acid may be placed in contact with the active surface to produce denaturation in a variety of ways. The active surface may be the surface of a membrane which may be a free thin layer or may be a layer on a solid support. The nucleic sample may be placed upon the membrane for a few seconds to produce denaturation and may then be removed. Where the active surface is provided by polymer beads, a sample of the nucleic acid may be run through a column of the beads suitable to provide a retention time of a few seconds so as to produce denaturation. The NAFION membrane may be applied as a coating on a surface such as the interior of a tube through which the liquid is run. For instance, the interior of a pipette tip may be coated, the liquid may be briefly drawn up into the pipette and then expelled to transform nucleic acid with liquid into single-stranded form.

If DNA is exposed to a NAFION membrane for a period in excess of a few seconds, adsorption of the DNA on to the NAFION surface occurs and the DNA may be damaged. It is known for instance, that low pH can cause depressurisation of DNA. Accordingly, it will normally be necessary to remove the nucleic acid containing solution from the membrane before this occurs. Preferably, after denaturation the pH of the solution is corrected to prevent damage to the nucleic acid. For instance, the denatured nucleic acid may be mixed with a suitable buffer. Alternatively, a surface of the opposite acidity or basicity may be used to reverse any pH change in the liquid.

The length of time for which the solution should remain in contact with the active surface will depend upon the nature of the surface. For example, NAFION membranes change in their activity according to age and storage conditions. Generally, the activity decreases upon storage, particularly if the membrane is allowed to adsorb water. If the activity of the surface is such that denaturation occurs inconveniently quickly, passing into the stage where adsorption of the DNA becomes a problem, the use of an aged surface with reduced activity may overcome this difficulty.

We have found that prewashing a NAFION membrane with buffered salt solution eliminates denaturation of a DNA solution subsequently contacted with the membrane, so this should be avoided. Prewashing with water is acceptable however.

reverse the effect of the active surface and allow renaturation of the nucleic acid to take place to produce the double-stranded form, either the liquid containing the nucleic acid may be removed from the active surface as described above or steps may be taken to negate the effect of the active surface. For instance, an electrode may be provided, optionally coated with the material providing the active surface, and a voltage may be applied to the electrode such as to negate the denaturing effect of the active surface. For instance, where the active surface is provided by a NAFION membrane coating over an electrode, a negative voltage may be applied to this electrode.

Cycles of renaturation and denaturation may be achieved by periods of the application of negative voltage in the case of acidic membranes or positive voltage in the case of basic membranes alternating with periods of zero voltage, reduced voltage, or reversed voltage.

A negatively charged electrode may also be used to draw nucleic acid by electrophoresis into contact with a membrane in or on which the electrode is positioned so that, at least when the voltage is turned off, denaturation occurs.

A polymerase chain reaction may be conducted in the presence of an active surface providing periods of denaturation and of renaturation of this kind.

The effect of the voltage may be such as to desorb any nucleic acid which has adsorbed to the active surface.

The invention will be further described and illustrated with reference to the accompanying drawings in which.

The invention will be illustrated by the following examples.

EXAMPLE 1

Figure 1:
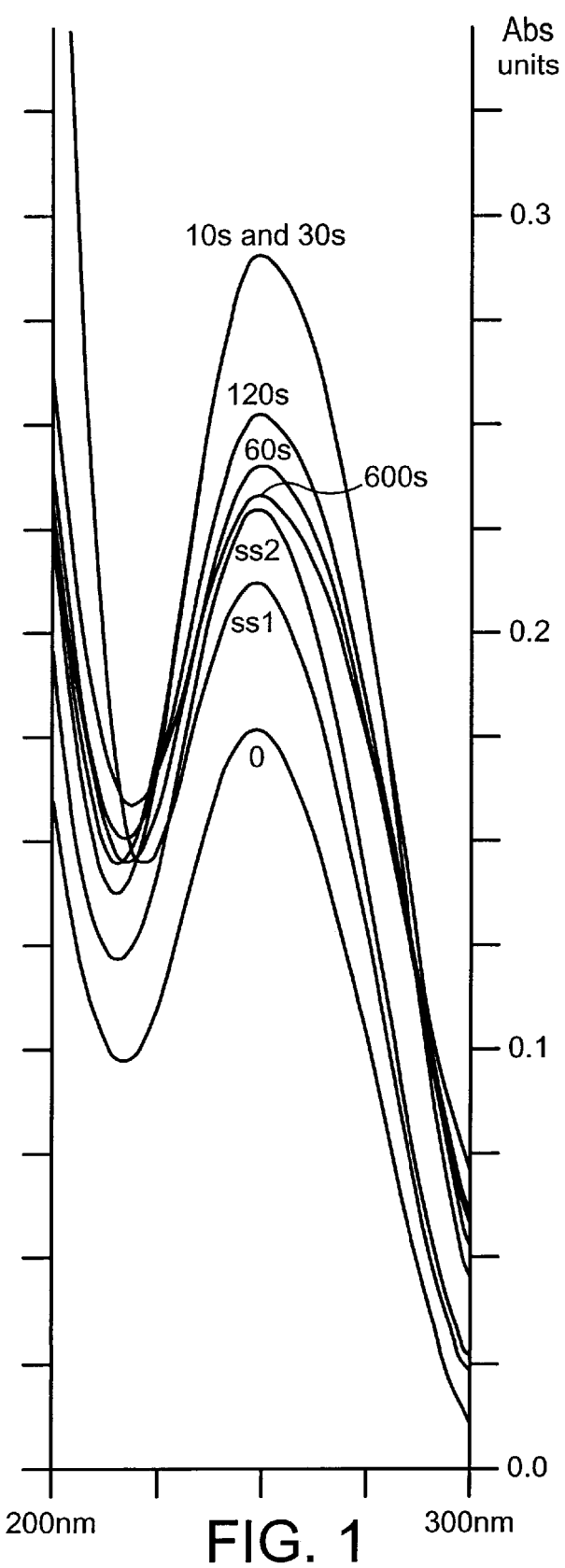
FIG. 1 shows hyperchromicity curves of calf thymus DNA in contact with a NAFION membrane surface for from 0 to 600 seconds.

A volume of 50 to 100 $\mu$l of a solution of 10 micrograms per ml calf thymus DNA (CtDNA) in water was placed on a NAFION 117 grade membrane. The DNA solution was pipetted on to the membrane and left for a measured period in the range 0 to 600 seconds before being removed by pipette and being placed in a microcuvette for spectrophotometric analysis by measurement of absorbence in the range 200 to 300 nm $\lambda$. The results appear in FIG. 1.

Figure 2:
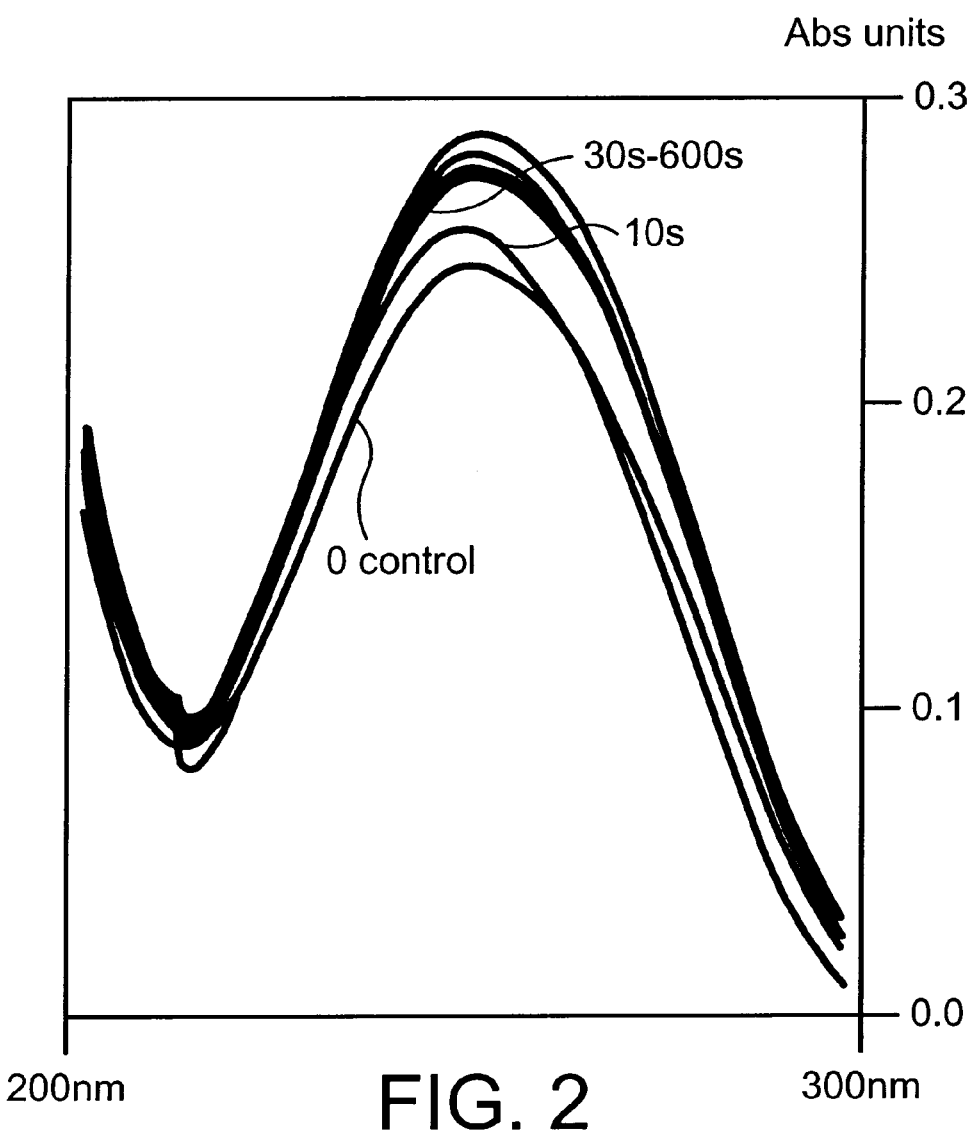
FIG. 2 shows similar curves for single-stranded calf thymus DNA exposed to a similar membrane for a similar period.

As a first control, the DNA was denatured by heat at 90° C. for 6 minutes and its absorbence as measured. The results of two repeats of this appear in FIG. 1 as cases SS1 and SS2. As a further control, the DNA was denatured by heat at 90° C. for 6 minutes and then placed on the NAFION membrane for a measured period in the same way as described for the double-stranded material. The results are shown in FIG. 2. It can be seen that whilst the hyperchromicity shift produced by NAFION exposure of dsDNA is pronounced and increases with exposure time to beyond that of heat denatured ssDNA after 10 seconds, the membrane produces little change in the absorbence of ssDNA. This is indicative of denaturation of the dsDNA to single-stranded form. After 30 seconds the absorbence of the double-stranded sample falls, perhaps due to adsorption on to the membrane. However, the membrane has little effect on the heat denatured DNA.

Comparison with FIG. 2 suggests that denaturation is complete after approximately 120 seconds. Further hyperchromicity shifts after that may be associated with changes which can occur in a single strand of DNA such as the opening of hairpin structures and the like.

NAFION as pellets or as a membrane has been found to be as effective for denaturising DNA as a temperature of 95° C. Moreover, for conducting SDA one needs to dilute 1:5 the salt solution of DNA that one starts with, this will not be necessary using NAFION.

EXAMPLE 2

The following is a suitable protocol for an amplification procedure according to the invention. To operate a strand displacement amplification (SDA) one may place a 10–100 $\mu$l sample (eg. 30 $\mu$l) of DNA solution (eg. 725 ng of linearised plasmid ($1.5 \times 10^{11}$ molecules) by pipette on to NAFION 117 membrane and mix for 10 to 60 s (eg. 30–45 seconds) by sucking in and out of the pipette tip or spreading over surface with a coverslip or simply stirring with the pipette tip end. A 1 $\mu$l aliquot is removed and added to the reaction mixture which is mixed and then left to incubate for the required amplification to occur. The reaction mixture may be as conventionally used in a strand displacement amplification.

The mechanism by which the denaturisation is produced is not known with certainty. NAFION is a cation exchanger. It accepts cations and releases protons, lowering the pH of 5 mM TRIS (pH 7.9), 12.5 nM KOAc, 2.5 mM MgOAc2 to pH=2–3 and perhaps denaturing DNA by protonating the N3 position of cytidine (pKa-4.2) and the N1 psotion of adenine (pKa-3.5). But it also denatures DNA in $H_2O$. A 30 µl aliquot of $H_2O$ containing 725 ng of plasmid (74 µM phosphates) contains 100–1000 µM cation associated with the DNA. If the DNA released all its cations to NAFION in exchange for protons, the resultant pH should drop to between 4 and 3. In practice, the pH drops to –5.5 which should be too high to permanently protonate cytidine or adenine. Perhaps the DNA denatures from phosphate repulsion after stripping of its cations, and/or there is transient protonation of the bases that disrupts hydrogen bonding.

However, whatever the mechanism at work may be, the efficacy of the technique is demonstrated by the results of the above procedure applied to the denaturation and amplification of DNA in the following examples.

EXAMPLE 3

Figure 3:
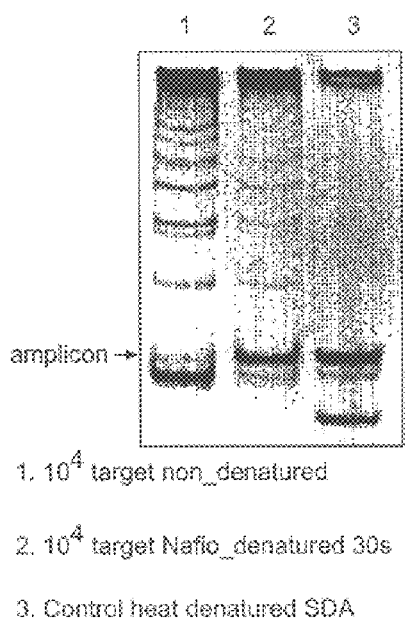
FIG. 3 shows a gel demonstrating successful SDA of DNA denatured on NAFION in Example 3.
Figure 4:
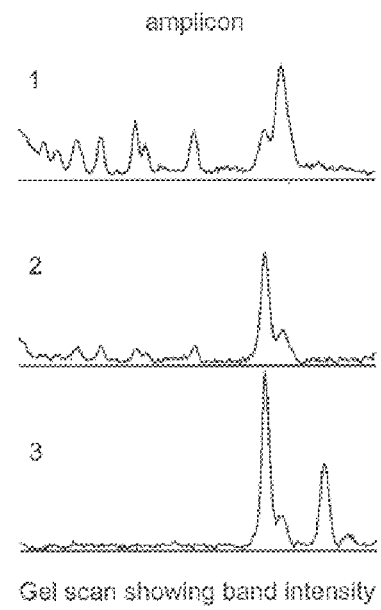
FIG. 4 shows band intensity readings based on the gel of FIG. 3.

$10^4$ molecules of double stranded calf thymus DNA were denatured on a NAFION membrane in accordance with Example 1 and subjected to SDA. The results are shown in FIGS. 3 and 4 where it can be seen that the amplicon band is substantially intense in run 2 using NAFION denaturation than in control run 1, without denaturation. The position of the amplicon band is demonstrated by the positive control run 3 using heat denaturation.

EXAMPLE 4

Figure 5:
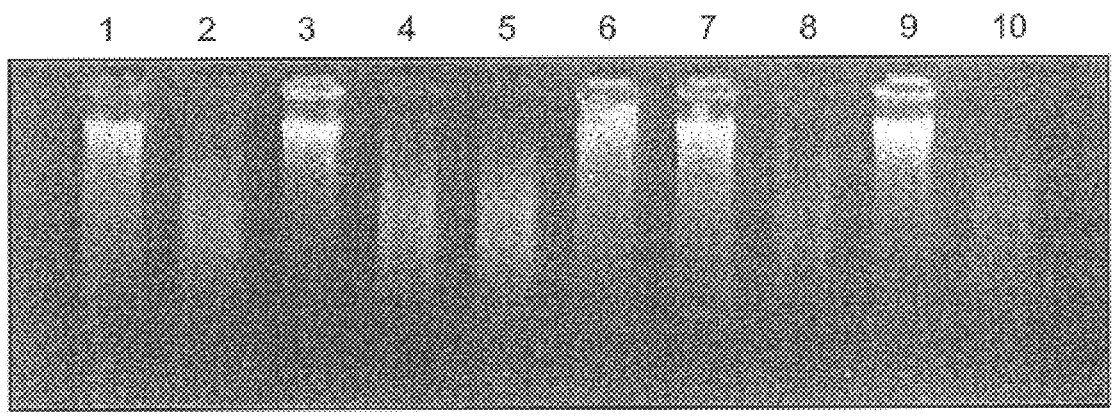
FIG. 5 shows a gel demonstrating denaturation of DNA on NAFION pellets as obtained in Example 4.

1 ml of double stranded calf thymus DNA (5 µg/ml) in water or in 10 mM Tris 1 mM ETDA buffer pH7.5 (TE) was incubated in the presence of 6 NAFION pellets (–0.25×0.5 cm) for 20 minutes or 60 minutes and the DNA was run on a gel to determine the degree of denaturation. As shown in FIG. 5, denaturation is seen in lanes 2, 4, 8 and 10 to a similar extent to that seen in positive control lane 5, and to a much greater extent than in negative control lanes 1, 3, 6, 7 and 9.

What is claimed is:

1. A method of denaturing or partially denaturing a double stranded nucleic acid, comprising contacting a solution comprising said double stranded nucleic acid with a surface having denaturation activity sufficient to produce said denaturation within a period of not more than one hour, wherein said surface comprises acid groups attached to an electron withdrawing polymer structure providing said surface with an acidity sufficient to produce said denaturation.

2. A method as claimed in claim 1, wherein the denaturation takes place within a period of not more than 5 minutes.

3. A method as claimed in claim 1, wherein the denaturation takes place within a period of not more than 1 minute.

4. A method as claimed in claim 1, wherein the denaturation takes place within a period of not more than 10 seconds.

5. A method as claimed in claim 1, wherein said electron withdrawing polymer structure comprises fluorine substituted carbon atoms.

6. A method as claimed in claim 1, wherein said polymer has a perfluorinated backbone structure.

7. A method as claimed in claim 6, wherein said polymer is a tetrafluoroethylene-perfluoro-2-(fluorosulphonylethoxy) propylvinyl ether.

8. A method of conducting a nucleic acid hybridisation procedure comprising denaturing a double stranded nucleic acid by a method as claimed in claim 1 to produce at least partially single stranded nucleic acid and hybridising a second nucleic acid with the single stranded nucleic acid so produced.

9. A method of conducting a nucleic acid amplification procedure requiring single stranded nucleic acid, comprising denaturing a double stranded nucleic acid by a method as claimed in claim 1, to produce at least partially single stranded nucleic acid and conducting said amplification using said single stranded nucleic acid so produced.

* * * * *